United States Patent [19]

Khanna

[11] Patent Number: 5,091,184
[45] Date of Patent: Feb. 25, 1992

[54] COATED ADHESIVE TABLETS

[75] Inventor: Satish C. Khanna, Bottmingen, Switzerland

[73] Assignee: Ciba-Geigy Corporation, Ardsley, N.Y.

[21] Appl. No.: 693,769

[22] Filed: Apr. 26, 1991

Related U.S. Application Data

[63] Continuation of Ser. No. 450,645, Dec. 14, 1989, abandoned.

[30] Foreign Application Priority Data

Dec. 30, 1988 [CH] Switzerland ............... 4855/88

[51] Int. Cl.$^5$ .................. A61K 9/20; A61K 9/28
[52] U.S. Cl. .................. 424/435; 424/474; 424/479; 424/482
[58] Field of Search .................. 424/479, 482

[56] References Cited

U.S. PATENT DOCUMENTS

| | | | |
|---|---|---|---|
| 3,972,995 | 8/1976 | Tsuk et al. | 424/435 |
| 4,156,013 | 5/1979 | Bruinvels et al. | 424/435 |
| 4,292,299 | 9/1981 | Suzuki et al. | 424/435 |
| 4,572,832 | 2/1986 | Kigasawa et al. | 424/435 |
| 4,801,460 | 1/1989 | Goertz et al. | 424/465 |
| 4,876,092 | 10/1989 | Mizobuchi et al. | 424/435 |
| 4,900,552 | 2/1990 | Sanvordeker et al. | 424/435 |

OTHER PUBLICATIONS

Chemical Abstracts 98:22818Y-Pharmaceutical Adhesive formulations for Treatment of Oral Mucosa Disorders 3/14/83.

American Heritage Dictionary. p. 1537 & p. 274.

Primary Examiner—Thurman K. Page
Assistant Examiner—Amy Hulina
Attorney, Agent, or Firm—Irving M. Fishman; Karen G. Kaiser

[57] ABSTRACT

The invention relates to a pharmaceutical composition for the application of baclofen, in the form of an adhesive tablet, to the mucosa in the oral cavity, which pharmaceutical composition comprises a) a hydrophilic tablet core, the top surface of which adheres to the receptor surface of the oral mucosa and which contains the drug baclofen or a pharmaceutically acceptable salt thereof and, as excipients, a swellable vinyl polymer, a galactomannan and/or a pharmaceutically acceptable wax and/or a glyceride or completely or partially hydrogenated glyceride, and further optional excipients, and if desired, b) a hydrophobic coating which covers the tablet core a), with the exception of the surface provided for the release of baclofen.

The invention further relates to a process for the preparation of this adhesive tablet and the therepeutic use thereof as spasmolytic.

8 Claims, No Drawings

COATED ADHESIVE TABLETS

This application is a continuation of application Ser. No. 450,645, filed Dec. 14, 1989 now abandoned.

The present invention relates to a pharmaceutical composition for the application of baclofen in the form of an adhesive tablet to the mucosa in the oral cavity, to a process for the preparation of said tablet, and to the therapeutic use thereof as spasmolytic.

Baclofen, i.e. 4-amino-3-(4-chlorophenyl)butyric acid (Lioresal®, Ciba-Geigy), can be used therapeutically as myotonolytic drug in the treatment of, for example, spasticity of the skeletal muscles in multiple sclerosis, and also of spinal-cord diseases of infectious, degenerative, traumatic or neoplasmatic origin, transverse myelitis and the like. Reference is made in this connection to the Red List No. 63008, Index of Formulated Drugs, Editio Cantor 1987, D-7690 Aulendorf. Commercially available dosage forms are tablets containing 5, 10 and 25 mg of active drug.

At the commencement of therapy with conventional tablets, side-effects including daytime sedation, nausea, vomiting, diarrhoea, dizziness and, occasionally, especially in elderly patients, psychotic states such as depressive mood disorders, may occur (q.v. Red List loc. cit.). Because of such side-effects, therapy consists in administering the drug initially in low doses, for example 5 mg three times daily to adults, and increasing the individual dosage at three day intervals by 5 mg three times daily until the optimum dosage level of 30–75 mg daily is reached.

Such dosage instructions have drawbacks. Increasing the number of times the drug is administered over the course of several days at the commencement of therapy and the frequent doses administered in the course thereof give rise to the risk of dosage errors being made by misuse of the directions, for example through omission of a dose or by prematurely taking too high a dose. Hence the error of overdosage as well as of underdosage may occur.

It is the object of the present invention to provide an improved dosage form for the administration of baclofen, which permits uniform administration at the commencement, as well as in the course, of therapy at constant intervals. The improved dosage form will also reduce the number of daily doses administered, preferably to one to two doses, and the dosage itself.

No other dosage forms such as capsules, dragées or syrups are suitable for attaining this object, as sufficient resorption of baclofen occurs only in the upper gastrointestinal tract, especially in the duodenum, after administration with these formulations. If in addition to rapid resorption the drug is also quickly metabolised, then the number of times the drug is administered and the dosage itself cannot be reduced.

Administration through the mucous membranes by means of buccal or sublingual formulations such as lozenges or adhesive tablets affords the advantage of partially or substantially by-passing the lower parts of the gastrointestinal tract and of prolonged release of the drug in the oral cavity.

A suitable dosage form for baclofen would have to ensure a continuous release of the drug over an extended period of time of more than 12 hours at a conventional dose of 25 mg or of more than six hours at lower doses, such that said dosage form would make it possible to reduce the number of doses administered while maintaining the same dosage, or to reduce the dosage while maintaining uniform administration of the drug.

Adhesive tape formulations can have disadvantages, as they take up a large amount of space when applied to the mucous membranes in the oral cavity and are felt by the patient to be an irritant. Adhesive tablets have the advantage of occupying a smaller space. However, such dosage forms, when applied to a smaller area, must have sufficient adhesive properties that they will remain affixed to the oral mucosa even when chewing, eating or moving the tongue, and yet can be easily removed, if necessary.

This object is achieved by the present invention which relates to a pharmaceutical composition for the application of baclofen, in the form of an adhesive tablet, to the mucosa in the oral cavity.

Said pharmaceutical composition comprises
a) a hydrophilic tablet core, the top surface of which adheres to the receptor surface of the oral mucosa and which contains the drug baclofen or a pharmaceutically acceptable salt thereof and, as excipients, a swellable vinyl polymer, a galactomannan and/or a pharmaceutically acceptable wax and/or a glyceride or completely or partially hydrogenated glyceride, and further optional excipients, and, if desired,
b) a hydrophobic coating which covers the tablet core a), with the exception of the surface provided for the release of baclofen.

This pharmaceutical composition has exceptional adhesive and release properties. As human bioavailability data show, after administration of the dosage form the plasma concentrations increase less strongly than after administration of conventional tablets. However, the drug concentration remains longer on a therapeutic level. The decrease in drug concentration occurs later. Because of its small size, the pharmaceutical composition can be applied to any sites in the oral cavity for adhesion to mucous membranes, especially to the palate, but may also buccally, lingually or sublingually, and the firm adhesion does not interfere with the ingestion of food. Owing to its pleasing taste, small size and elasticity in the swollen state, the adhesive tablet is not felt to be an irritant. The patient is not conscious of the presence of the tablet and even "forgets" it. The adhesive tablet makes it possible to reduce the number of doses administered. At a dosage of 25 mg, the administration of two to three doses daily will suffice, for the supply of drug is continuous. The release of therapeutically effective amounts of drug at night is also ensured.

The terms and expressions used throughout this specification are defined as follows within the scope of this invention.

The hydrophilic tablet core is adhesive and able to absorb water or saliva. A portion of the drug is released to this fluid and carried with it to the gastrointestinal tract. A further portion passes through the oral mucosa direct into the bloodstream.

A pharmaceutically acceptable salt of baclofen is preferably an addition salt with a suitable acid, for example a dilute aqueous hydrohalic acid such as hydrochloric acid or hydrobromic acid. A preferred addition salt is the hydrochloride. The preparation of baclofen and salts thereof is disclosed, for example, in U.S. Pat. No. 3,634,428.

A swellable vinyl polymer expands when acted upon by water or saliva at body temperature, is elastic and is water-soluble at the pH of saliva. The polymer begins to dissolve slowly upon and after the rapid swelling. Subject to the composition and the degree of polymerisation of the vinyl polymer, this latter dissolves partially or completely while it adheres to the oral mucosa.

A swellable vinyl polymer is preferably a hydrophilic polymer of acrylic acid, methacrylic acid or esters thereof, a copolymer of acrylic acid, methacrylic acid or esters thereof, a copolymer of methacrylic acid or esters thereof, a copolymer of methacrylates or a polymeric aliphatic or cyclic vinyl amide.

A hydrophilic polymer of acrylic acid has preferably an average molecular weight of ca. $8.0 \times 10^5$ to $1.0 \times 10^6$, and is used in pharmacy as an excipient under the non-proprietory name Carbomer. Especially preferred are polymers which are sold by Goodrich under the registered trademark CARBOPOL 934 and are of pharmaceutical quality, for example CARBOPOL 934 P.

Hydrophilic polymers of methacrylic acid and esters thereof, copolymers of methacrylic acid and esters thereof, as well as copolymers of methacrylates preferably have an average molecular weight of ca. $8.0 \times 10^5$ to $1.0 \times 10^6$. The acid groups are partially or completely replaced by $C_1$-$C_4$alkyl groups, especially methyl or ethyl groups, which ester groups may in turn be substituted by hydrophilic groups, preferably trimethylammoniumethyl groups.

Such polymers are obtainable under the registered trademark EUDRAGIT from Röhm Pharma, Weiterstadt, Federal Republic of Germany. Especially preferred are swellable, permeable types such as EUDRAGIT NE 30 D. The use of types like EUDRAGIT L, S, RN or RS enables a slow release to be achieved.

A swellable vinyl polymer is also a polymeric aliphatic or cyclic vinyl amide, for example poly-N-vinyl-methylacetamide, poly-N-ethylvinylacetamide, poly-N-vinylmethyl-propionamide, poly-N-vinylethylpropionamide, poly-N-vinylmethylisobutyramide, poly-N-vinyl-2-pyrrolidone, poly-N-vinyl-2-piperidone, poly-N-vinyl-ε-caprolactam, poly-N-5-methyl-2-pyrrolidone or poly-N-vinyl-3-methyl-2-pyrrolidone, or poly-N-vinyl-2-pyrrolidone having an average molecular weight of ca. 10 000 to 700 000, or a copolymer of the cited aliphatic and cyclic vinylamides, for example the copolymer of vinyl-2-pyrrolidone and vinyl acetate, or a hydrolysis product thereof, for example the copolymer of vinyl-2-pyrrolidone and vinyl alcohol, in which the vinyl alcohol component has a degree of hydrolysis of 85-98%.

The preferred swellable vinyl polymer is poly-N-vinyl-2-pyrrolidone which has an average molecular weight of 20 000 to 700 000, is commercially available under the registered trademark Kollidon ® (BASF), and has the following properties: Soluble in water, ethanol, methanol, isopropanol, propylene glycol, methylene chloride, insoluble in ether, hydrocarbons, strongly hygroscopic (water absorption ca. 33% from ca. 70% rel. humidity), q.v. Pharmazeutische Technologie, Sucker H., et al., Thieme Verlag Stuttgart 1978, page 339.

A suitable swellable vinyl polymer is also the copolymer of vinyl pyrrolidone and vinyl acetate which has a monomer ratio of vinyl pyrrolidone to vinyl acetate of ca. 60:40 (% by weight) and has the following properties:

Purity: 95% (remainder: water), insoluble in ether and aliphatic hydrocarbons, very readily soluble in water, ethyl and isopropyl alcohol, methylene chloride, glycerol and 1,2-propylene glycol, pH of a 10% aqueous solution 3-5, viscosity (in 10% aqueous solution: 5 mPa.s), q.v. H.P. Fiedler, Lexikon der Hilfsstoffe, Editio Cantor 1982.

Such copolymers of vinyl pyrrolidone and vinyl acetate are known and/or can be obtained in a manner known per se in any ratio of the monomers. The 60:40 copolymer is, for example, commercially available under the registered trademark Kollidon ® VA 64 (BASF).

A galactomannan is a polysaccharide which is present in the endosperm cells of luguminosae and is used as pharmaceutical excipient. A preferred galactomannan is a cold water soluble galactomannan (25° C.) which has a Brookfield viscosity higher than 1000 [mPa sec] (measured in demineralised aqueous solution at 25° C., hydration time 1-24 hours and stirring at 20 rpm = revolutions per minute), and which is known by trivial names such as locust bean gum, guar gum or tara gum.

A particularly preferred galactomannan is that sold under the registered trademark Meyprogat ® by Meyhall, CH-8280 Kreuzlingen, more particularly the types MEYPROGAT 30, 60, 90 and 120 and, most preferably, MEYPROGAT 150.

A pharmaceutically acceptable wax consists essentially of mixtures of esters of linear carboxylic acids of ca. 18 to 34 carbon atoms with linear alcohols of about the same chain length, which esters are solid or semi-solid at room temperature. Preferred waxes are those of natural, preferably vegetable, origin which contain the said esters as main components (more than 50%) and, as further components, the free acids and alcohols derived from the esters, as well as lactones, lactides, hydrocarbons, sterols and the like.

A pharmaceutically acceptable wax is also a synthetic ester of linear carboxylic acids of ca. 10 to 20 carbon atoms and linear alcohols of about the same chain length, which esters are liquid at room temperature, a mixture of said synthetic esters, optionally with the cited waxes of natural origin, paraffin wax containing more than 20 carbon atoms, and a synthetic mixture of polyethylene glycols known under the name Carbowax.

Waxes of natural origin are waxes of animal or vegetable origin known as Cera flava (yellow wax, beeswax), Cera alba (bleached wax), Cera subliquids (viscous wax), propolis (bee glue), carnauba wax, Chinese wax, Japan wax, afridi wax, candellila wax, ghetta wax, godang wax, cape berry wax, myrtle wax, okuba wax, pisang wax, raphi wax or cetina.

A synthetic ester of linear carboxylic acids of ca. 10 to 20 carbon atoms and linear alcohols of about equal chain length, which ester is liquid at room temperature, is typically oleoyl oleate (DAB 7) or decyl oleate, for example the commercial forms sold by Henkel Co. under the registered trademark CETIOL, and the analogs commercially available under the trade names CETIOL A, B, LC and SN.

Paraffin wax (DAB 7) containing more than 20 carbon atoms consists essentially of a mixture of saturated hydrocarbons, preferably containing up to 30 carbon atoms in the chain, which mixture is solid at room temperature.

Carbowax is the name given to a mixture of synthetic polyethylene glycols which have a molecular weight of more than 600 and which at room temperature are semi-solid (ointment-like) or wax-like solids. Carbowaxes which are solid at room temperature and have a molecular weight above 400 are preferred.

A glyceride consists essentially of a mixture of natural origin or of an isolated natural or synthetic, substantially pure single component of an ester, which is present in said mixture, of glycerol with one equivalent (monoglyceride), two equivalents (diglyceride) or three equivalents (triglyceride) of unsaturated or saturated fatty acids containing ca. 4 to 30 carbon atoms, which are in the liquid or semi-solid, preferably solid, state at room temperature.

A completely or partially hydrogenated glyceride consists of a mixture of natural origin containing esters of glycerol with unsaturated fatty acids or of a synthetic, substantially pure single component of an ester, which is present in said mixture, of glycerol with unsaturated fatty acids which have been subjected to known hydrogenation, for example catalytically with hydrogen.

Mixtures of natural origin with the cited glycerides are typically the liquid, semi-solid and solid purified mixtures of vegetable origin, for example seeds or fruit, or of animal origin, and which are known trivially as oils, tallows and fats.

Such mixtures are, for example, the products described in national and supranational pharmacopeias, for example the European Pharmacopeia, as Olea piguia (neutralised fatty oils), especially oils for injection purposes, avocado oil, babassu oil, cotton-seed oil, Borneo tallow, beechnut oil, ground nut oil, mutton tallow, hazel nut oil, hydnocarpus oils, wood oil, cocoa butter, kapoka oil, coconut fatty or coconut oil, pumpkin oil, cod-liver oil, bay oil, corn oil, almond oil, miglyol oils, poppy oil, mowrah butter, olive oil, palm kernel fatty or palm-nut oil, palm oil, peach kernel oil, rape oil, castor oil, beef tallow, safflower oil, sesame oil, shea butter, softisan, soybean oil, sunflower oil, tee seed oil or walnut oil.

A completely or partially hydrogenated glyceride is preferred, for example obtainable by partial or complete hydrogenation of the cited natural mixtures such as the products sold under the name hydrogenated groundnut oil, hard fat, for example mixtures of monoesters, diesters and triesters of palmitic and stearic acid with glycerol, for example the products sold under the registered trademark PRECIROL (Gattefossé SA, France), or hydrogenated castor oil, for example the products which are commercially available under the registered trademarks CUTINA and CEROXIN (Henkel), CASTORWAX and OPALWAX (Baker Castor Oil Co., USA), CENWACHS (W. C. Hardesty, N.Y. USA), or CETYNOL (Givaudan, Geneva CH).

Further pharmaceutically acceptable excipients are those customarily used in tabletting for the preparation of granules, for example binders, lubricants, glidants, dispersants, fillers and the like. Thus it is possible to use conventional adjuvants such as lactose, saccharose, sorbitol, mannitol, starch, for example potato starch, corn starch or amylopectin, or cellulose, preferably microcrystalline cellulose, or magnesium stearate, in addition to the cited excipients.

The hydrophobic coating b) covers the tablet core a), with the exception of the non-coated surface provided for application. This non-covered surface of the coated tablet is applied and adheres to the oral mucosa. The non-coated surface is on the top- or underside of the tablet and may be of a different colour from the colour of the coating.

The hydrophobic coating itself, in contrast to the hydrophilic core, absorbs body fluid such as saliva only slowly. As it swells, the coating expands uniformly so that the neutral taste of the tablet, especially the feeling of softness and smoothness, is retained, and the taste of the components of the tablet core is masked.

Adjustment of the adhesive tablet, even when swollen, to the oral mucosa is thereby achieved, so that it can be applied almost everywhere in the oral cavity.

The tablet core a) is coated with the hydrophobic coating b) preferably in film coating thickness, for example ca. 0.01-0.1 mm. Suitable substances for the film layer are film-forming pharmaceutical waxes or polymers which can be applied from an organic solution or from an aqueous dispersion, and which are able to form water-insoluble or poorly water-soluble yet porous films, for example the above mentioned waxes, polyethylene glycols, ethyl cellulose, polyvinyl acetate, cellulose acetate, a mixture of polyvinyl pyrrolidone or a copolymer of polyvinyl pyrrolidone or a copolymer of polyvinyl pyrrolidone and polyvinyl acetate with hydroxypropylmethyl cellulose, polymeric epoxides, copolymers of alkylene oxide and alkyl glycidyl ethers, polylactic acid derivatives and the like. Also suitable are all film-layer materials (membranes) known in the literature which have porous properties, for example mixtures of water-insoluble acrylates such as copolymers of acrylates and methacrylates of the EUDRAGIT type (Röhm Pharma) which are applied in aqueous dispersion.

Preferred film-forming wax-like polymers are those selected from the group consisting of the ethylene oxide homopolymers known as polyethylene glycol (PEG) or polyethylene oxide, preferably polyethylene glycol having an average molecular weight of 2000 to 20 000, for example PEG 2000, 3000, 4000, 6000 and 8000. These polymers are sold by different manufacturers under various trade names.

To enhance the taste and also to increase porosity, the coating b) may additionally contain water-soluble additives such as sugar, for example saccharose or lactose, or aromatic substances.

The present invention relates preferably to a pharmaceutical composition in the form of an adhesive tablet, wherein a) the hydrophilic tablet core contains the drug baclofen, a swellable vinyl polymer which is a polymer of acrylic acid having an average molecular weight of ca. $8.0 \times 10^5$ to $1.0 \times 10^6$, a vinyl pyrrolidone polymer or a copolymer of vinyl pyrrolidone and vinyl acetate, a galactomannan which is a cold water soluble galactomannan (25° C.) having a Brookfield viscosity greater than 1000 [mPa sec] and/or a pharmaceutically acceptable wax, and b) the hydrophobic coating consists of polyethylene glycol having film-forming properties and optionally contains a sugar.

A further preferred embodiment of the invention relates to a pharmaceutical composition in the form of an adhesive tablet, wherein a) the hydrophilic tablet core contains the drug baclofen, a swellable vinyl polymer which is a polymer of acrylic acid having an average molecular weight of ca. $8.0 \times 10^5$ to $1.0 \times 10^6$, a vinyl pyrrolidone polymer or a copolymer of vinyl pyrrolidone and vinyl acetate, a galactomannan which is a cold water soluble galactomannan (25° C.) having a Brookfield viscosity greater than 1000 [mPa sec] and a completely or partially hydrogenated glyceride, for example hydrogenated castor oil, and/or a pharmaceutically acceptable wax, and b) the hydrophobic coating consists of polyethylene glycol having film-forming properties and optionally contains a sugar.

The present invention relates most particularly to a pharmaceutical composition in the form of an adhesive tablet, wherein a) the hydrophilic tablet core contains the drug baclofen, a swellable vinyl polymer which is a polymer of acrylic acid having an average molecular weight of ca. $8.0 \times 10^5$ to $1.0 \times 10^6$, guar gum as galactomannan, and a completely or partially hydrogenated glyceride, and the hydrophobic coating b) consists of polyethylene glycol having an average molecular weight greater than 4000 and optionally saccharose. The pharmaceutical composition of the present invention is suitable as myotonolytic for the treatment of spasticity in multiple sclerosis, and also of muscle spasms in spinal diseases of infectious or degenerative genesis, for example in spastic spinal paralysis, amyotrophic lateral sclerosis or syringomyelia. The tablets are administered in the dosage prescribed for baclofen, for example 5, 10 or 25 mg. It is preferred to administer 1-2 tablets containing 25 mg of drug daily. The therapeutic use of the pharmaceutical composition as myonolytic is also an object of the present invention.

The pharmaceutical composition of this invention is prepared by known tabletting and coating methods. The method comprises compressing a granular formulation containing the components of the core a), or preparing the hydrophilic tablet core a) by compacting the components, with or without the addition of glidants, and, if desired, providing said core with the hydrophobic coating b), with the exception of the surface left free for the release of the active drug.

The pharmaceutical composition is preferably prepared by compressing a granular formulation which is obtained, for example, by sieving and, if desired, by comminuting the drug, with or without the excipients, compacting or wet grinding with a solvent such as ethanol or water, removing the solvent or drying, with or without the addition of lubricants or glidants such as magnesium stearate, comminuting the granules and sieving once more.

The granules can be compressed to tablet cores in a conventional tabletting machine, for example an EKO Korsch eccentric tabletting machine, at a pressure of ca. 10 kN. Coating can be effected by applying an aqueous-ethanolic solution in which, for example, polyethylene glycol and saccharose is dissolved or dispersed. Preferably one side of the tablet will remain free from coating.

The pharmaceutical composition may vary in form and be, for example, round, oval, oblong, cylindrical and the like, and may also vary in size depending on the concentration of drug. It may also be transparent, colourless or coloured, and can also be marked so as to impart to this product an individual appearance and to make it immediately recognisable. The use of dyes can serve to enhance the appearance as well as to identify the composition. Suitable dyes for use in pharmacy are, for example, carotinoids, iron oxides or chlorophylls.

EXAMPLE 1

| | |
|---|---|
| Baclofen (LIORESAL) | 25.00 mg |
| MEYPROGAT 150 | 42.16 mg |
| CARBOPOL 934 P | 22.39 mg |
| magnesium stearate | 0.45 mg |
| demineralised water | 15 ml |

The baclofen, which is ground to an average particle size of 0.5 mm, MEYPROGAT and CARBOPOL are sieved through a 0.8 mm round sieve and the components are mixed for 10 minutes in a TURBULA planetary mixer. A small amount of water is added to the mixture, and the moist mixture is then forced through a 2.0 mm round sieve and dried for 1 hour at 40° C. under vacuum. The granules, which have a residual moisture content of 6.31%, are comminuted by being forced through a 0.8 mm round sieve and, after addition of magnesium stearate, finally forced through the 0.8 mm round sieve. The resultant granular formulation is mixed for 3 minutes in the planetary mixer and tabletted in an EKO Korsch eccentric tabletting machine. Compression force: ca. 10 kN; die: diameter ca. 7.00 mm. The tablet cores are coated on one side with a film-coating mixture consisting of 44 g of polyethylene glycol 8000, 29 g of saccharose, 52 g of demineralised water, and 22 g of ethanol.

EXAMPLE 2

| | mg per core |
|---|---|
| Phase I | |
| baclofen | 25.00 |
| Meyprogat ® 150 | 30.10 |
| Cutina ® HR (hydrogenated castor oil) | 12.99 |
| Carbopol ® 200 | 21.64 |
| Phase II: | |
| Aerosil ® 200 | 0.27 |
| | 90.00 |

The components of phase I are forced through a 0.8 mm sieve and mixed for 10 minutes in a Turbula mixer. The mixture is compacted at 50 kg/cm² to give 0.7 mm platelets. The platelets are ground over a 0.8 mm sieve. The outer phase II is added to the inner phase I over a 0.8 mm sieve and both phases are mixed for 5 minutes in the Turbula mixer.

The granular formulation so obtained is compressed in a single die tabletting machine at a compression force of 16 kN using a die of 7.00 mm diameter.

The resultant adhesive tablets adhere well to the palate and are soluble in vivo over ca. 12-15 hours.

What is claimed is:

1. A pharmaceutical composition for the application of baclofen, in the form of an adhesive tablet, to the mucosa in the oral cavity, which pharmaceutical consists essentially of a hydrophobic tablet core, the top surface of which adheres to the receptor surface of the oral mucosa and which consists essentially of the drug baclofen or a pharmaceutically acceptable salt thereof and, as excipients, a swellable vinyl polymer, a galactomannan and at least one pharmaceutically acceptable excipient selected from the group consisting of a wax, a glyceride, a completely hydrogenated glyceride and a partially hydrogenated glyceride.

2. A pharmaceutical composition according to claim 1, wherein the swellable vinyl polymer in the hydrophilic tablet core a) is an acrylic acid polymer having an average molecular weight of ca. $8.0 \times 10^5$ to $1.0 \times 10^6$, a vinyl pyrrolidone polymer or a copolymer of vinyl pyrrolidone and vinyl acetate.

3. A pharmaceutical composition according to claim 2, wherein the swellable vinyl polymer in the hydrophilic tablet core a) is an acrylic acid polymer having an average molecular weight of ca. $8.0 \times 10^5$ to $1.0 \times 10^6$, or polyvinyl pyrrolidone having an average molecular weight of ca. 20 000 to 70 000.

4. A pharmaceutical composition according to claim 1, wherein the galactomannan in the hydrophilic tablet core a) is a cold water soluble galactomannan (25° C.) which has a Brookfield viscosity higher than 1000 [mPa sec] (measured in demineralised aqueous solution at 25° C., hydration time 1-24 hours, 20 rpm).

5. A pharmaceutical composition according to claim 4, wherein the cold water soluble galactomannan in the hydrophilic tablet core a) is guar gum.

6. The composition of claim 1 further comprising at least one additional pharmaceutically acceptable excipient.

7. A pharmaceutical composition for the application of baclofen, in the form of an adhesive tablet, to the mucosa in the oral cavity, said pharmaceutical consisting essentially of:

a) a hydrophobic tablet core, the top surface of which adheres to the receptor surface of the oral mucosa and which consists essentially of the drug baclofen or a pharmaceutically acceptable salt thereof and, as excipients, a swellable vinyl polymer, a galactomannan and at least one pharmaceutically acceptable excipient selected from the group consisting of a wax, a glyceride, a completely hydrogenated glyceride and a partially hydrogenated glyceride; and b) a hydrophobic coating which covers the tablet core with the exception of the surface provided for the release of baclofen.

8. A pharmaceutical composition according to claim 7, wherein the hydrophobic coating consists of polyethylene glycol having film-forming properties and a sugar.

* * * * *